United States Patent
Park et al.

(10) Patent No.: US 11,565,997 B2
(45) Date of Patent: Jan. 31, 2023

(54) METHOD FOR PREPARING DICARBAMATE COMPOUNDS FROM DIAMINES AND THE CATALYST THEREOF

(71) Applicant: KOREA RESEARCH INSTITUTE OF CHEMICAL TECHNOLOGY, Daejeon (KR)

(72) Inventors: Ji Hoon Park, Daejeon (KR); Tae Sun Chang, Daejeon (KR); Young Woo You, Daejeon (KR); Iljeong Heo, Daejeon (KR); Jin Hee Lee, Daejeon (KR); Seul Gi Han, Daejeon (KR); Kwan Yong Jeong, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 229 days.

(21) Appl. No.: 16/768,866

(22) PCT Filed: Nov. 19, 2018

(86) PCT No.: PCT/KR2018/014200
§ 371 (c)(1),
(2) Date: Oct. 30, 2020

(87) PCT Pub. No.: WO2019/107818
PCT Pub. Date: Jun. 6, 2019

(65) Prior Publication Data
US 2022/0002236 A1    Jan. 6, 2022

(30) Foreign Application Priority Data
Dec. 1, 2017   (KR) .................. 10-2017-0164393

(51) Int. Cl.
C07C 269/04    (2006.01)
B01J 23/10     (2006.01)
B01J 23/44     (2006.01)

(52) U.S. Cl.
CPC ............. *C07C 269/04* (2013.01); *B01J 23/10* (2013.01); *B01J 23/44* (2013.01)

(58) Field of Classification Search
None
See application file for complete search history.

(56) References Cited

U.S. PATENT DOCUMENTS

| 3,979,427 A | 9/1976 | Ottmann et al. |
| 4,474,978 A | 10/1984 | Drent et al. |
| 7,022,871 B2 * | 4/2006 | Chaudhari ............ C07C 269/04 560/25 |

FOREIGN PATENT DOCUMENTS

| JP | S60149552 | * | 8/1985 | ............ C07B 61/00 |
| KR | 100277207 B1 | | 1/2001 | |

(Continued)

OTHER PUBLICATIONS

ZSM-5-Zeolite Socony Mobil-5(downloaded from https://www.acsmaterial.com/blog-detail/zsm-5-molecular-seive.html on Jun. 30, 2022 ) (Year: 2022).*

(Continued)

*Primary Examiner* — Amy C Bonaparte
(74) *Attorney, Agent, or Firm* — STIP Law Group, LLC

(57) ABSTRACT

The present invention relates to a method of directly preparing a dicarbamate compound from a diamine compound, and more particularly to a method of directly preparing a dicarbamate compound by reacting a diamine compound with an alcohol compound in the presence of a mixed gas of carbon monoxide (CO) and oxygen ($O_2$) using a Pd/MO$_x$ (Continued)

catalyst configured such that a palladium (Pd) active metal is supported on a metal oxide or metalloid oxide carrier.

8 Claims, 1 Drawing Sheet

(56) References Cited

FOREIGN PATENT DOCUMENTS

| KR | 1020110039971 A | 4/2011 |
|----|-----------------|--------|
| KR | 1020150134970 A | 12/2015 |
| KR | 1020160018697 A | 2/2016 |
| KR | 101719757 B1 | 3/2017 |

OTHER PUBLICATIONS 10.6: Gas Mixtures and Partial Pressures (downloaded from https://chem.libretexts.org/Bookshelves/General_Chemistry/Map%3A_Chemistry_-_The_Central_Science_(Brown_et al.)/10%3A_Gases/10.06%3A_Gas_Mixtures_and_Partial_Pressures on Jun. 30, 2022) (Year: 2022).*

Shi ("A Novel PdCI2/ZrO2-SO42—Catalyst for Synthesis of Carbamates by Oxidative Carbonylation of Amines" Journal of Catalysis 203, 525-528, 2001) (Year: 2001).*

International Search Report of PCT/KR2018/014200, Mar. 5, 2019, English translation.

* cited by examiner

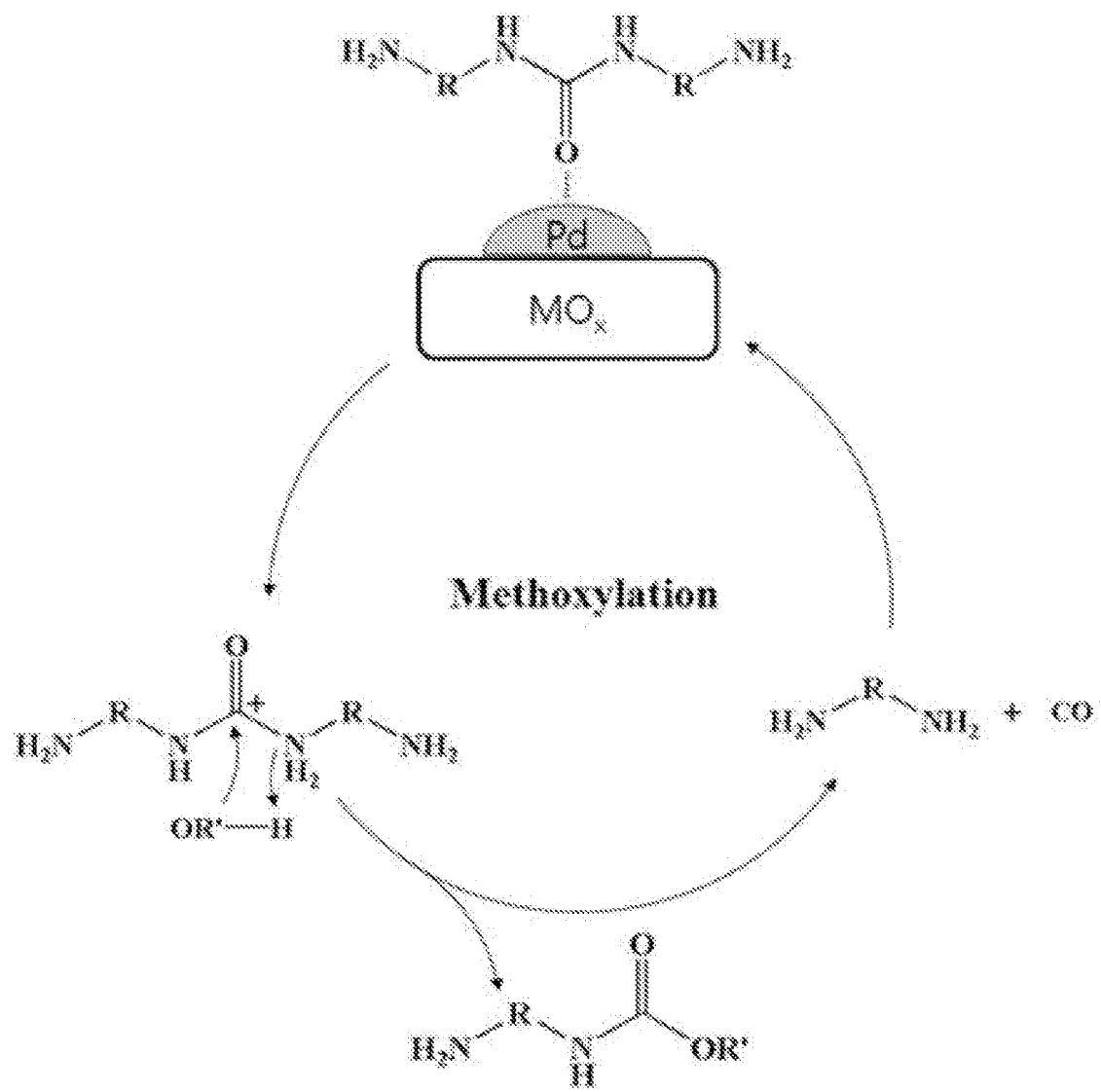

METHOD FOR PREPARING DICARBAMATE COMPOUNDS FROM DIAMINES AND THE CATALYST THEREOF

CROSS-REFERENCE TO RELATED APPLICATIONS

This application is the U.S. National Phase under 35 U.S.C. § 371 of International Application No. PCT/KR2018/014200 filed on Nov. 19, 2018, which in turn claims the benefit of Korean Application No. 10-2017-0164393, filed on Dec. 1, 2017, the disclosures of which are incorporated by reference into the present application.

TECHNICAL FIELD

The present invention relates to a method of directly preparing a dicarbamate compound from a diamine compound, and more particularly to a method of directly preparing a dicarbamate compound by reacting a diamine compound with an alcohol compound in the presence of a mixed gas of carbon monoxide (CO) and oxygen ($O_2$).

BACKGROUND ART

A dicarbamate compound, which is a compound represented by R—$(NHCOOR')_2$, may be converted into a diisocyanate compound through thermal decomposition. Therefore, dicarbamate is used as a raw material or an intermediate of pesticides, pharmaceuticals or polyurethane.

Carbamates (urethane compound) such as alkyl carbamate are organic compounds that are conventionally useful as raw material for pharmaceuticals, pesticides, etc., as raw material for purification chemistry, as analytical reagents for alcohols, or as an industrial material having a wide range of end uses. Moreover, the use of alkyl carbamate as a raw material for the preparation of isocyanate without the use of phosgene is being recently studied.

Isocyanate is widely used as a raw material for polyurethane and is industrially produced through the reaction of amine and phosgene (a phosgene method). However, since phosgene is highly toxic and corrosive and inconvenient to handle, an environmentally friendly method for producing isocyanate by first preparing carbamate and then thermally decomposing the carbamate thus obtained has recently been proposed to replace the phosgene method.

Methods of preparing carbamate through environmentally friendly processes are as follows. For example, there are methods of reacting a nitro compound or amine with carbon monoxide and an alcohol at a high temperature under high pressure in the presence of a catalyst, methods of synthesizing carbamate through reaction of amine and dialkyl carbonate, methods of reacting amine with ethylene or propylene carbonate, and methods of synthesizing carbamate through two steps, namely reacting amine with urea to afford alkylurea, which is then reacted with alcohol. Among the general synthesis methods described above, the method of using carbon monoxide uses, as a reactant, a greenhouse gas, which is a major cause of global warming, and interest therein has recently increased.

Korean Patent No. 10-1719757 discloses a method of directly preparing a monocarbamate compound by reacting a monoamine compound with an alcohol compound in the presence of a mixed gas of carbon monoxide (CO) and oxygen ($O_2$) using a Pd/HY-zeolite catalyst configured such that a palladium (Pd) active metal is supported on a HY-zeolite carrier in which the $SiO_2/Al_2O_3$ molar ratio is adjusted (Patent Document 01). Here, based on the results of synthesis of monocarbamate using HY-zeolite, carbon, alumina ($Al_2O_3$), silica ($SiO_2$), etc. as the carrier of Pd, the carbamate selectivity appears in the order of HY-zeolite>carbon>silica ($SiO_2$)>alumina ($Al_2O_3$). In the case of HY-zeolite, it has been reported that the generation of urea as a reaction byproduct is drastically lowered.

Korean Patent No. 10-0277207 discloses the use of a selenium (Se) compound selected from among $M_2SeO_3$, $M_2Se_2O_5$ and $(CH_3O)Se(O)(OM)$ [in which M is an alkali metal element] as a catalyst when preparing a carbamate compound by reacting an amine compound with an alcohol compound in the presence of a mixed gas of carbon monoxide and oxygen. However, the selenium compound used above is a homogeneous catalyst, and thus it is not easy to separate the catalyst from the reaction mixture, and there are problems related to the high toxicity of selenium (Patent Document 02).

U.S. Pat. No. 3,979,427 discloses the use of a palladium or rhodium catalyst and a cocatalyst including a metal halide such as iron chloride for increasing the reaction rate when preparing carbamate using a nitro or amine compound, but the cocatalyst, which is used in excess, is difficult to separate after reaction and may cause the device to corrode (Patent Document 03).

U.S. Pat. No. 4,474,978 discloses a method of preparing carbamate by reacting primary amine or urea with an aromatic nitro compound in the presence of CO and alcohol using a catalyst based on palladium including $PdCl_2$ and a phosphine ligand joined thereto through coordination bonding, but the catalyst is extremely expensive, and it is not easy to recover the catalyst after the reaction (Patent Document 04).

As confirmed in the aforementioned related documents, the study on the oxidative carbonylation reaction for preparing carbamate was mainly performed on monocarbamate, and not many studies have been performed on the preparation of dicarbamate.

Moreover, the technology for preparing monocarbamate and the technology for preparing dicarbamate differ from each other. The reason thereof is as follows: in the preparation of monocarbamate, urea is formed as an intermediate during the oxidative carbonylation reaction, whereas in the case of diamine, which is a raw material for the preparation of dicarbamate, polyurea is formed as an intermediate product of the oxidative carbonylation reaction, unlike the preparation of monocarbamate. Here, the polyurea is not readily converted into dicarbamate, with the undesirable result that the reaction yield of the final product dicarbamate is lowered. Hence, it is difficult to apply the catalyst system for the preparation of monocarbamate as a catalyst for the preparation of dicarbamate, and moreover, in the synthesis of a dicarbamate compound, it is necessary to develop a catalyst composition suitable for inhibiting polyurea formation and to study reaction conditions, unlike monocarbamate.

The present inventors have performed intensive and extensive studies on techniques for preparing dicarbamate using palladium active metal in the oxidative carbonylation reaction, thus culminating in the present invention.

DISCLOSURE

Technical Problem

Accordingly, the present invention has been made keeping in mind the problems encountered in the related art, and an objective of the present invention is to provide a catalyst system capable of preparing dicarbamate at high yield and a method of preparing dicarbamate from diamine using the same.

The other detailed purposes of the present invention will be clearly understood by those skilled in the art through the specific content set forth below.

Technical Solution

In order to accomplish the above objective, the present invention provides a method of preparing a dicarbamate compound, including reacting reactants including carbon monoxide (CO), oxygen ($O_2$), a diamine compound and an alcohol compound using a catalyst configured such that a palladium (Pd) active metal is supported on a metal oxide or metalloid oxide carrier.

Also, in an embodiment of the present invention, the palladium (Pd) active metal may be supported in an amount of 1 to 5 wt % on the metal oxide or metalloid oxide carrier.

Also, in an embodiment of the present invention, the metal oxide or metalloid oxide is preferably at least one selected from among cerium oxide ($CeO_2$), silica ($SiO_2$) and alumina ($Al_2O_3$), and is more preferably cerium oxide ($CeO_2$).

Also, in an embodiment of the present invention, the catalyst may be used in an amount of 10 to 50 wt % based on the amount of the diamine compound.

Also, in an embodiment of the present invention, in the method of preparing the dicarbamate compound according to the present invention, a cocatalyst may be further used in addition to the catalyst, and the cocatalyst may be alkali metal iodide.

Also, in an embodiment of the present invention, the cocatalyst may be used in an amount of 0 to 80 wt % based on the amount of the diamine compound.

Also, in an embodiment of the present invention, the diamine compound may be represented by Chemical Formula 1 below.

R—(NH$_2$)$_2$      [Chemical Formula 1]

(In Chemical Formula 1, R represents C1-C18 alkanediyl, C3-C20 cycloalkanediyl, C6-C24 aryldiyl, or a linker represented by Structural Formula 1 below:

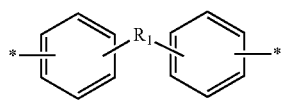

[Structural Formula 1]

in Structural Formula 1, R$_1$ represents C1-C18 alkanediyl, and "-*" represents a site binding to a nitrogen (N) atom in Chemical Formula 1.)

Also, in an embodiment of the present invention, the alcohol compound may be represented by Chemical Formula 2 below.

R'OH      [Chemical Formula 2]

(In Chemical Formula 2,

R' represents a C1-C18 alkyl group, a C3-C8 cycloalkyl group, a benzyl group, or a phenyl group.)

Also, in an embodiment of the present invention, the molar ratio b/a of carbon monoxide (b) relative to oxygen (a) may be 2 to 20.

Also, in an embodiment of the present invention, the reaction may be carried out at a temperature of 110° C. to 150° C. under a pressure of 1 to 50 atm for 1 to 12 hr.

In order to accomplish the above objective, the present invention provides a catalyst for preparing a dicarbamate compound, suitable for use in the reaction for preparing a dicarbamate compound from reactants including carbon monoxide (CO), oxygen ($O_2$), a diamine compound and an alcohol compound, in which the catalyst may be configured such that a catalytically active metal is supported on a metal oxide or metalloid oxide carrier.

Also, in an embodiment of the present invention, the catalytically active metal may include Pd.

Also, in an embodiment of the present invention, the metal oxide or metalloid oxide is preferably at least one selected from among cerium oxide ($CeO_2$), silica ($SiO_2$) and alumina ($Al_2O_3$), and is more preferably cerium oxide ($CeO_2$).

Also, in an embodiment of the present invention, the palladium (Pd) active metal may be supported in an amount of 1 to 5 wt % on the metal oxide or metalloid oxide carrier.

Advantageous Effects

When using a catalyst according to the present invention, a dicarbamate compound can be obtained at high yield from a diamine compound. Moreover, a method of preparing dicarbamate according to the present invention uses a heterogeneous catalyst, making it easy to separate the catalyst after the reaction.

In addition, a catalyst for preparing a dicarbamate compound according to the present invention and a preparation method using the same make it possible to exhibit catalytic activity even at relatively low pressure, thus generating economic benefits.

BRIEF DESCRIPTION OF DRAWING

The FIGURE shows a mechanism for preparing dicarbamate using a Pd/MO$_x$ catalyst according to the present invention, in which the Pd$^{2+}$ component of the palladium element present on the catalyst exhibits catalytic activity that accelerates the methoxy substitution reaction.

MODE FOR INVENTION

Unless otherwise defined, all technical and scientific terms used herein have the same meanings as those typically understood by those skilled in the art to which the present invention belongs. Generally, the nomenclature used herein is well known in the art and is typical.

As used herein, when any part is said to "comprise" or "include" any element, this does not mean that other elements are excluded, and such other elements may be further included unless otherwise specifically mentioned.

The present invention pertains to a method of preparing a dicarbamate compound from a diamine compound through W oxidative carbonylation of alcohol.

As shown in Scheme 1 below, a diamine compound may be converted into dicarbamate through oxidative carbonylation of alcohol.

[Scheme 1]

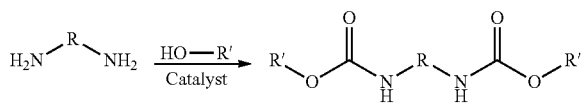

In Scheme 1, R represents C1-C18 alkanediyl, C3-C20 cycloalkanediyl, C6-C24 aryldiyl, or a linker represented by Structural Formula 1 below.

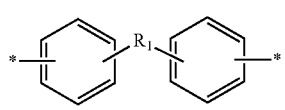

[Structural Formula 1]

In Structural Formula 1, $R_1$ represents C1-C18 alkanediyl, and "-*" represents a site binding to a nitrogen (N) atom in Chemical Formula 1.

Also, R' represents a C1-C18 alkyl group, a C3-C8 cycloalkyl group, a benzyl group, or a phenyl group.

Also, the diamine compound may be prepared into various compounds through oxidative carbonylation of alcohol, depending on the reaction conditions. As shown in Scheme 2 below, as an intermediate product, polyurea, which is a polymerizable material, is generated, undesirably resulting in a decreased reaction yield.

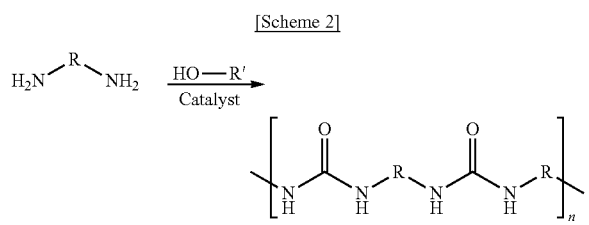

[Scheme 2]

In Scheme 2, R and R' are as defined in Scheme 1.

The present invention is intended to provide a catalyst system capable of maximizing the selectivity of the desired dicarbamate compound by inhibiting the generation of polyurea, which is an intermediate product of the oxidative carbonylation, and a method of preparing a dicarbamate compound using the same.

Specifically, the present invention pertains to a method of preparing a dicarbamate compound including reacting a diamine compound with an alcohol compound in the presence of a mixed gas of carbon monoxide (CO) and oxygen ($O_2$), using a reaction catalyst, particularly a Pd/$MO_x$ catalyst configured such that a palladium (Pd) active metal is supported on a metal oxide or metalloid oxide carrier ($MO_x$).

The method of preparing the dicarbamate compound according to the present invention is specified below.

In the preparation method of the present invention, a dicarbamate synthesis reaction is carried out, using a diamine compound and an alcohol compound as reactants, in the presence of a mixed gas of carbon monoxide (CO) and oxygen ($O_2$), using a catalyst, particularly a Pd/$MO_x$ catalyst configured such that a palladium (Pd) active metal is supported on a metal oxide or metalloid oxide carrier. Here, carbon monoxide (CO) and oxygen ($O_2$) also participate in the reaction, and may thus be regarded as reactants.

In the preparation method of the present invention, the diamine compound, serving as the reactant, may be represented by Chemical Formula 1 below.

R—$(NH_2)_2$     [Chemical Formula 1]

In Chemical Formula 1, R represents C1-C18 alkanediyl, C3-C20 cycloalkanediyl, C6-C24 aryldiyl, or a linker represented by Structural Formula 1 below.

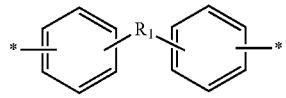

[Structural Formula 1]

In Structural Formula 1, $R_1$ represents C1-C18 alkanediyl, and "-*" represents a site binding to a nitrogen (N) atom in Chemical Formula 1.

Specific examples of the diamine compound represented by Chemical Formula 1 may include, but are not limited to, 1,2-ethanediamine (EDA), 1,3-propanediamine (PDA), 1,4-butanediamine (BDA), 1,6-hexanediamine (HDA), 1,8-octanediamine (ODA), 1,2-cyclohexanediamine (1,2-CHDA), 1,3-cyclohexanediamine (1,3-CHDA), 1,4-cyclohexanediamine (1,4-CHDA), 1,2-cyclohexane bismethylamine (1,2-CHBMA), 1,3-cyclohexane bismethylamine (1,3-CHBMA), 1,4-cyclohexane bismethylamine (1,4-CHBMA), isophorone diamine (IPDA), 4,4'-methylenebiscyclohexylamine (H12MDA), m-xylenediamine (MXDA), o-xylenediamine (OXDA), p-xylenediamine (PXDA), 2,6-toluenediamine, 2,4-toluenediamine, 4,4'-methylenedianiline, and the like.

Also, the alcohol compound, serving as the reactant, may be represented by Chemical Formula 2 below.

R'OH     [Chemical Formula 2]

In Chemical Formula 2, R' represents a C1-C18 alkyl group, a C3-C8 cycloalkyl group, a benzyl group, or a phenyl group.

Specific examples of the alcohol compound represented by Chemical Formula 2 may include n-propanol, n-butanol, isobutanol, n-pentanol, n-hexanol, 2-ethylhexanol, n-octanol, cyclohexanol, methylcyclohexanol, benzyl alcohol, 2-methoxyethanol (MEG), 2-ethoxyethanol (EEG), 2-propoxyethanol (PEG), 2-isopropoxyethanol, 2-butoxyethanol (BEG), 3-methoxypropanol (MPG), 2-(2-methoxyethoxy)ethanol (MEEG), 2-(2-ethoxyethoxy)ethanol (EEEG), 2-(2-butoxyethoxy) ethanol (BEEG), diethylene glycol monomethyl ether (MDEG), diethylene glycol monoethyl ether (EDEG), diethylene glycol monobutyl ether (BDEG), triethylene glycol monomethyl ether (MTEG), triethylene glycol monoethyl ether (ETEG), triethylene glycol monobutyl ether (BTEG), tetraethylene glycol monomethyl ether (MTTEG), tetraethylene glycol monoethyl ether (ETTEG), and the like. In view of reactivity, an alcohol having 1 to 4 carbon atoms is preferably used.

In the present invention, the alcohol compound, serving as the reactant, may be used in an amount of 2 to 800 moles, and preferably 100 to 800 moles relative to 1 mole of the diamine compound. If the alcohol compound is used in an amount less than 2 moles, the reaction may not proceed efficiently due to the lack of alcohol required for the methoxylation reaction. On the other hand, if the amount thereof exceeds 800 moles, side reactions may be promoted, undesirably lowering selectivity.

In the preparation method of the present invention, used is a palladium-supported catalyst, particularly a Pd/$MO_x$ (in which M is a metal or metalloid) catalyst in which a palladium (Pd) active metal is supported on a metal oxide or metalloid oxide carrier. When the catalyst thus configured is used, as shown in FIGURE, the $Pd^{2+}$ component of the palladium element supported on the metal oxide or metalloid oxide carrier may accelerate the methoxy substitution reaction of urea, thereby producing carbamate and inhibiting the formation of polyurea, ultimately making it possible to obtain dicarbamate at high yield.

A Pd/MO$_x$ catalyst configured such that the palladium (Pd) active metal is supported in an amount of 1 to 5 wt % on the metal oxide or metalloid oxide carrier is preferably used. If the amount of the palladium active metal that is supported is less than 1 wt %, the reactivity may decrease. On the other hand, if the amount thereof exceeds 5 wt %, the particle size of the supported metal may increase, and thus reactivity may be deteriorated.

The metal oxide or metalloid oxide carrier is preferably at least one selected from among cerium oxide (CeO$_2$), silica (SiO$_2$) and alumina (Al$_2$O$_3$), and more preferably cerium oxide (CeO$_2$) in view of increasing the reaction yield. Here, the metal or metalloid oxide carrier does not include zeolite.

The Pd/MO$_x$ catalyst is used in an amount of 10 to 50 wt %, and preferably 20 to 30 wt %, based on the amount of the diamine compound. If the amount of the catalyst is less than 10 wt %, the reaction efficiency may be decreased or the reaction rate may be greatly lowered. On the other hand, if the amount thereof exceeds 50 wt %, the catalyst may be used in excess, thus negating economic benefits.

In the preparation method of the present invention, it is possible to prepare dicarbamate through oxidative carbonylation using a Pd/MO$_x$ catalyst alone configured such that a palladium (Pd) active metal is supported on a metal oxide or metalloid oxide carrier. Here, the Pd/MO$_x$ catalyst is a heterogeneous catalyst, thus facilitating separation thereof after the reaction.

Moreover, in the preparation method of the present invention, the Pd/MO$_x$ catalyst is used as a main catalyst, and a cocatalyst may be used. The cocatalyst may include alkali metal iodide, for example, NaI, KI, CsI, etc.

The cocatalyst is used in an amount of 0 to 80 wt %, and preferably 10 to 50 wt %, based on the amount of the diamine compound, in order to achieve desired effects. If the amount of the cocatalyst exceeds 80 wt %, the dicarbamate yield may be decreased.

In the preparation method of the present invention, a mixed gas of carbon monoxide (CO) and oxygen (O$_2$) is used, and in consideration of reactivity and explosiveness of the mixed gas, the molar ratio b/a of carbon monoxide (b) relative to oxygen (a) may be 2 to 20. If the b/a molar ratio is less than 2, the catalyst may be oxidized and thus inactivated. On the other hand, if the b/a molar ratio exceeds 20, the reaction rate may be lowered due to the lack of the oxidant, undesirably lowering the dicarbamate yield.

Also, the reaction pressure in the presence of CO/O$_2$ mixed gas is preferably 1 to 50 atm, and more preferably 10 to 30 atm in view of economic benefits. The catalyst of the present invention and the reaction conditions set forth above are preferable taking into consideration productivity and device costs because catalytic activity may be exhibited even under low pressure of the CO/O$_2$ mixed gas.

The method of preparing the dicarbamate compound is performed under the above conditions. Here, the reaction temperature may vary depending on the type of diamine compound serving as the reactant. In consideration of the reaction rate and the dicarbamate selectivity, the reaction temperature is appropriately set within the range of 110 to 150° C. If the reaction temperature is lower than 110° C., the yield of the reaction product may be remarkably lowered. On the other hand, if the reaction temperature is higher than 150° C., dicarbamate production efficiency may be decreased due to the promotion of polyurea generation.

Also, the reaction may be carried out for 1 to 12 hr, and preferably 5 to 10 hr, in consideration of the dicarbamate yield and economic benefits of the reaction.

In addition, the present invention pertains to a catalyst for preparing a dicarbamate compound using reactants including carbon monoxide (CO), oxygen (O$_2$), a diamine compound and an alcohol compound, the catalyst being configured such that a palladium (Pd) active metal is supported on a metal oxide or metalloid oxide carrier.

Preferably, the metal oxide or metalloid oxide carrier is at least one selected from among cerium oxide (CeO$_2$), silica (SiO$_2$) and alumina (Al$_2$O$_3$).

The palladium (Pd) active metal may be supported in an amount of 1 to 5 wt % on the metal oxide or metalloid oxide carrier.

In the following description of exemplary embodiments of the present invention, detailed descriptions of known functions and components incorporated herein will be omitted when the same may make the subject matter of the present invention unclear.

Specific structural and functional descriptions of embodiments and drawings of the present invention disclosed herein are only for purposes of illustration of the preferred embodiments of the present invention, and are not intended to represent the entire technical scope of the present invention, and thus a variety of equivalents and modifications able to substitute therefor may be provided at the point of time of filing of the present invention.

Hereinafter, the reaction for preparing dicarbamate using a catalyst according to the present invention is described through the following examples and comparative examples.

<Example 1> Synthesis of Toluene Dicarbamate (TDC) from Toluene Diamine (TDA)

0.5 mmol of toluene diamine, 16 ml of methanol, 30 mg of 2.5 wt % Pd/CeO$_2$, and 37 mg of NaI were placed in a 100 ml high-pressure reactor, after which a CO/O$_2$ mixed gas (CO/O$_2$=4) was allowed to flow thereto so that the pressure was adjusted to 10 bar, followed by stirring at 500 rpm for 5 hr at 135° C., thus synthesizing toluene dicarbamate.

[Reaction Scheme 1]

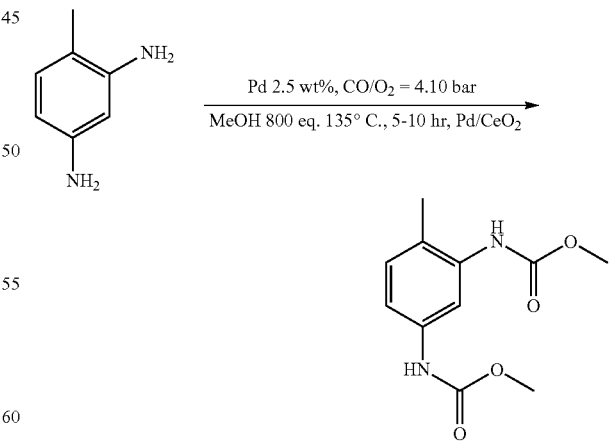

After termination of the reaction, the reaction mixture was cooled to room temperature, added with dimethyl naphthalene, serving as an external standard, and analyzed through NMR. The diamine conversion and the toluene dicarbamate yield were calculated using Equations 1 and 2 below. The results thereof are shown in Table 1 below. In the following Equations 1 and 2, "substrate" represents diamine.

$$\text{Diamine conversion (\%)} = \left(1 - \frac{\text{substrate remaining after reaction (mmol)}}{\text{initially added substrate (mmol)}}\right) * 100 \quad \text{[Equation 1]}$$

$$\text{Dicarbamate yield (\%)} = \left(\frac{\text{produced dicarbamate (mmol)}}{\text{initially added substrate (mmol)}}\right) * 100 \quad \text{[Equation 2]}$$

<Examples 2 and 3 and Comparative Examples 1 to 3>

A catalytic reaction for synthesizing toluene dicarbamate from toluene diamine was carried out in the same manner as in Example 1, and the synthesis yields of toluene dicarbamate using palladium supported on different carriers were compared, and the results thereof are shown in Table 1 below.

In the following Table 1, "HY" represents Y-zeolite, and "C" represents activated carbon.

TABLE 1

| No. | Catalyst | Diamine conversion [%] | Dicarbamate yield [%] |
|---|---|---|---|
| Example 1 | Pd/CeO$_2$ | >99 | 77.9 |
| Example 2 | Pd/SiO$_2$ | >99 | 62.7 |
| Example 3 | Pd/Al$_2$O$_3$ | >99 | 58.0 |
| Comparative Example 1 | PdCl$_2$ | >99 | 15.2 |
| Comparative Example 2 | Pd/HY | >99 | 19.0 |
| Comparative Example 3 | Pd/C | >99 | 46.7 |

As is apparent from Table 1, when synthesizing toluene dicarbamate using Pd/CeO$_2$ as the catalyst, the maximum yield of 77.9% was obtained for a reaction time of 5 hr, which was about 15% higher than when using Pd/SiO$_2$ exhibiting the second-highest activity, indicating that the yield was increased by about 24% or more based on the yield when using Pd/SiO$_2$, thus indicating industrial usefulness.

When preparing toluene dicarbamate using PdCl$_2$, which is a representative homogenous catalyst among catalysts for use in the preparation of monocarbamate through oxidative carbonylation, the yield thereof was very low, specifically 15.2% (in which the synthesis yield of monocarbamate using PdCl$_2$ under conditions similar to those in the above Examples was 90% or more). In this regard, since the catalyst in the production of W monocarbamate shows different results compared to the production of dicarbamate, it can be found that the catalyst for dicarbamate production must be designed differently from the catalyst for monocarbamate production.

The yield of toluene dicarbamate (TDC) was greatly increased in all of the Examples using the Pd/MO$_x$ catalyst as the catalyst system of the present invention, unlike the Comparative Examples.

<Examples 4 to 8> Synthesis Yield of Toluene Dicarbamate (TDC) Depending on Time Toluene dicarbamate was synthesized under the same conditions as in Example 1, with the exception that the reaction time was changed. The synthesis yields of toluene dicarbamate depending on the reaction time were compared, and the results thereof are shown in Table 2 below.

TABLE 2

| No. | Reaction time [hr] | Diamine conversion [%] | Dicarbamate yield [%] |
|---|---|---|---|
| Example 4 | 2 | >99 | 62.28 |
| Example 5 | 4 | >99 | 73.40 |
| Example 6 | 6 | >99 | 88.67 |
| Example 7 | 8 | >99 | 91.68 |
| Example 8 | 10 | >99 | 95.57 |

As is apparent from Table 2, when the reaction time was increased up to 10 hr in the state in which the reaction conditions were fixed at 10 atm, toluene dicarbamate was capable of being produced at a high yield of 95.57%.

<Examples 9 and 10> Synthesis of Methylene Diphenyl Dicarbamate (MDC) from Methylenedianiline (MDA)

0.5 mmol of methylenedianiline, 16 ml of methanol, 30 mg of 2.5 wt % Pd/CeO$_2$, and 37 mg of NaI were placed in a 100 ml high-pressure reactor, after which a CO/O$_2$ mixed gas (CO/O$_2$=4) was allowed to flow thereto so that the pressure was set to 10 bar, followed by stirring at 500 rpm at 135° C., thus synthesizing methylene diphenyl dicarbamate.

A catalytic reaction for synthesizing methylene diphenyl dicarbamate was carried out under the same conditions as in Example 1, with the exception that methylenedianiline was used in lieu of toluene diamine. The reaction results depending on changes in the reaction time are shown in Table 3 below.

[Reaction Scheme 2]

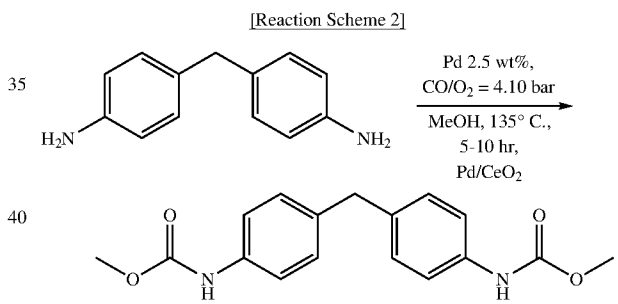

TABLE 3

| No. | Reaction time [hr] | Diamine conversion [%] | Dicarbamate yield [%] |
|---|---|---|---|
| Example 9 | 5 | >99 | 90.58 |
| Example 10 | 10 | >99 | >99 |

As is apparent from Table 3, when the reaction was carried out for 5 hr using 2.5 wt % Pd/CeO$_2$, the yield of methylene diphenyl dicarbamate was 90.58%. Also, when the reaction time was increased up to 10 hr under the same conditions, a high methylene diphenyl dicarbamate yield of 99% or more was obtained.

<Example 11> Synthesis of Toluene Dicarbamate (TDC) Not Using Cocatalyst 0.5 mmol of toluene diamine, 16 ml of methanol, and 30 mg of 2.5 wt % Pd/CeO$_2$ were placed in a 100 ml high-pressure reactor, after which a mixed CO/O$_2$ gas (CO/O$_2$=4) was allowed to flow thereto so that the pressure was set to 10 bar, followed by stirring at 500 rpm for 5 hr at 135° C., thus synthesizing toluene dicarbamate.

After termination of the reaction, the reaction mixture was cooled to room temperature, added with dimethyl naphthalene, serving as an external standard, and analyzed through NMR. The diamine conversion and the dicarbamate yield were calculated using Equations 1 and 2.

TABLE 4

| No. | Catalyst | Diamine conversion [%] | Dicarbamate yield [%] |
|---|---|---|---|
| Example 11 | 2.5 wt % Pd/CeO$_2$ | >99 | 30 |

As is apparent from Table 4, when toluene dicarbamate was synthesized in the presence of the Pd/CeO$_2$ catalyst alone without use of the NaI cocatalyst, a yield of 30% within a reaction time of 5 hr could be obtained even in the state in which the cocatalyst was not used.

Although the embodiments of the present invention have been disclosed for illustrative purposes with reference to the accompanying drawings, those skilled in the art will appreciate that various modifications and equivalents are possible without departing from the scope and spirit of the invention as disclosed in the accompanying claims. Therefore, the scope of the present invention should be determined by the accompanying claims.

INDUSTRIAL APPLICABILITY

When the catalyst according to the present invention is used, a dicarbamate compound can be obtained at high yield from a diamine compound. In addition, the method of preparing dicarbamate according to the present invention uses a heterogeneous catalyst, thus facilitating separation of the catalyst after the reaction. In addition, the catalyst for the preparation of dicarbamate and the preparation method using the same according to the present invention make it possible to exhibit catalytic activity even at relatively low pressure, thus generating economic benefits and being industrially applicable.

The invention claimed is:

1. A method of preparing a dicarbamate compound, comprising:
    reacting reactants comprising carbon monoxide (CO), oxygen (O$_2$), a diamine compound, and an alcohol compound using a catalyst configured such that a palladium (Pd) active metal is supported on a metal oxide carrier, wherein the metal oxide carrier is cerium oxide (CeO$_2$).

2. The method of claim 1, wherein the palladium (Pd) active metal is supported in an amount of 1 to 5 wt % on the metal oxide carrier.

3. The method of claim 1, wherein the catalyst is used in an amount of 10 to 50 wt % based on an amount of the diamine compound.

4. The method of claim 1, further comprising the use of an alkali metal iodide cocatalyst.

5. The method of claim 4, wherein the alkali metal iodide cocatalyst is used in an amount of 80 wt % or less based on an amount of the diamine compound.

6. The method of claim 1, wherein the diamine compound is represented by Chemical Formula 1 below, and the alcohol compound is represented by Chemical Formula 2 below:

R—(NH$_2$)$_2$         [Chemical Formula 1]

wherein, in Chemical Formula 1, R represents C1-C18 alkanediyl, C3-C20 cycloalkanediyl, C6-C24 aryldiyl, or a linker represented by Structural Formula 1 below:

[Structural Formula 1]

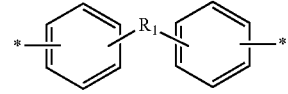

wherein, in Structural Formula 1, R$_1$ represents C1-C18 alkanediyl, and "-*" represents a site binding to a nitrogen (N) atom in Chemical Formula 1; and R'OH         [Chemical Formula 2]

wherein, in Chemical Formula 2, R' represents a C1-C18 alkyl group, a C3-C8 cycloalkyl group, a benzyl group, or a phenyl group.

7. The method of claim 1, wherein a molar ratio (b/a) of the carbon monoxide (b) relative to the oxygen (a) is 2 to 20.

8. The method of claim 1, wherein the reacting is carried out at a temperature of 110° C. to 150° C. under a pressure of 1 to 50 atm for 1 to 12 hr.

* * * * *